US00PP15729P2

(12) United States Plant Patent
Hoogendoorn

(10) Patent No.: US PP15,729 P2
(45) Date of Patent: Apr. 26, 2005

(54) ***ALSTROEMERIA* PLANT NAMED 'ZALSAMANO'**

(50) Latin Name: *Alstromeria hybrida*
Varietal Denomination: Zalsamano

(75) Inventor: Cornelis Arie Hoogendoorn, Aarlanderveen (NL)

(73) Assignee: Van Zanten Plants B.V., Hillegom (NL)

( * ) Notice: Subject to any disclaimer, the term of this patent is extended or adjusted under 35 U.S.C. 154(b) by 16 days.

(21) Appl. No.: 10/602,081

(22) Filed: Jun. 23, 2003

(51) Int. Cl.[7] ..... A01H 5/00
(52) U.S. Cl. ..... Plt./309
(58) Field of Search ..... Plt./309

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Alstroemeria* plant named 'Zalsamano', characterized by its erect and strong flowering stems; vigorous growth habit; intense golden yellow-colored flowers; and good postproduction longevity.

1 Drawing Sheet

Botanical classification/cultivar designation: *Alstroemeria hybrida* cultivar Zalsamano.

BACKGROUND OF THE INVENTION

The present Invention relates to a new and distinct cultivar of *Alstroemeria* plant, botanically known as *Alstroemeria hybrida*, commercially used as a cut flower *Alstroemeria*, and hereinafter referred to by the name 'Zalsamano'.

The new *Alstroemeria* is a product of a planned breeding program conducted by the Inventor in Rijnsburg, The Netherlands. The objective of the breeding program was to develop new cut flower *Alstroemeria* cultivars with desirable flower and plant qualities, attractive flower colors and excellent postproduction longevity.

The new *Alstroemeria* originated from a cross-pollination made by the Inventor in June, 1997 in Rijnsburg, The Netherlands, of a proprietary *Alstroemeria hybrida* selection identified as 96411-004, not patented, as the female, or seed, parent with a proprietary *Alstroemeria hybrida* selection identified as 97915-004PN, not patented, as the male, or pollen, parent. The new *Alstroemeria* was discovered and selected by the Inventor as a flowering plant within the progeny of the stated cross-pollination in a controlled environment in Rijnsburg, The Netherlands in 1998.

Asexual reproduction of the new cultivar by root divisions in a controlled environment in Rijnsburg, The Netherlands, since September, 1998, has shown that the unique features of this new *Alstroemeria* are stable and reproduced true to type in successive generations of asexual propagation.

SUMMARY OF THE INVENTION

Plants of the cultivar Zalsamano have not been observed under all possible environmental conditions. The phenotype may vary somewhat with variations in environment such as temperature and light intensity without, however, any variance in genotype.

The following traits have been repeatedly observed and are determined to be the unique characteristics of 'Zalsamano'. These characteristics in combination distinguish 'Zalsamano' as a new and distinct cultivar:

1. Erect and strong flowering stems.
2. Vigorous growth habit.

3. Intense golden yellow-colored flowers.
4. Good postproduction longevity.

Plants of the new *Alstroemeria* can be compared to plants of the parent selections. In side-by-side comparisons conducted in Rijnsburg, The Netherlands, plants of the new *Alstroemeria* differed from plants of the parent selections primarily in flower color as plants of the parent selections had yellow-colored flowers.

Plants of the new *Alstroemeria* can be compared to plants of the cultivar Zalsasenan, disclosed in a U.S. Plant patent application filed concurrently. In side-by-side comparisons conducted in Rijnsburg, The Netherlands, plants of the new *Alstroemeria* differed from plants of the cultivar Zalsasenan in the following characteristics:

1. Plants of the new *Alstroemeria* had narrower inflorescences but larger flowers than plants of the cultivar Zalsasenan.
2. Plants of the new *Alstroemeria* and the cultivar Zalsasenan differed in flower color.
3. Plants of the new *Alstroemeria* had shorter peduncles and pedicels than plants of the cultivar Zalsasenan.

Plants of the new *Alstroemeria* can be compared to plants of the cultivar Stajello, not patented. In side-by-side comparisons conducted in Rijsenhout, The Netherlands, plants of the new *Alstroemeria* differed from plants of the cultivar Stajello in the following characteristics:

1. Plants of the new *Alstroemeria* had longer flowering stems than plants of the cultivar Stajello.
2. Plants of the new *Alstroemeria* produced fewer flowering stems per year than plants of the cultivar Stajello.

BRIEF DESCRIPTION OF THE PHOTOGRAPH

The accompanying colored photograph illustrates the overall appearance of the new *Alstroemeria,* showing the colors as true as it is reasonably possible to obtain in colored reproductions of this type. Colors in the photograph may differ slightly from the color values cited in the desired botanical description which accurately describe the colors of the new *Alstroemeria.* The photograph comprises a side perspective view of a typical flowering stems of 'Zalsamano'.

DETAILED BOTANICAL DESCRIPTION

The aforementioned photograph, following observations and measurements describe plants of the new *Alstroemeria* grown in Rijsenhout, The Netherlands in a glass-covered greenhouse in ground beds. During the production of the plants, day temperatures ranged from 15 to 25° C., night temperatures ranged from 10 to 15° C. and light levels averaged 5,000 lux. Plants used for the photograph and description were about one year old. The photograph and the description were taken during August and September, 2002. Color references are made to The Royal Horticultural Society Colour Chart, 1995 Edition, except where general terms of ordinary dictionary significance are used.

Botanical classification: *Alstroemeria hybrida* cultivar Zalsamano.

Parentage:

*Female parent.*—Proprietary *Alstroemeria hybrida* selection identified as 96411-004, not patented.

*Male parent.*—Proprietary selection of *Alstroemeria hybrida* identified as 97915-004PN, not patented.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 10 to 30 cm. Diameter: About 3 to 10 mm. Texture: Smooth. Color: Close to 155D.

Plant description:

*Plant habit.*—Upright; freely branching, bushy appearance.

*Vigorous growth habit.*—

*Time from planting to harvest of cut flowers.*—About 80 to 90 days.

*Number of flowering stems produced per year.*—About 204 to 220.

*Plant height.*—About 154 to 200 cm.

*Plant diameter* (*spread*).—About 30 to 35 cm.

*Flowering stem description.*—Aspect: Erect. Length: About 150 cm. Diameter: About 4.6 to 8 mm. Internode length: About 2.5 to 5.5 cm. Strength: Strong. Texture: Glabrous. Color: Close to 144A.

*Foliage description.*—Leaves asymmetrical; sessile. Length: About 11 to 20 cm. Width: About 3.5 to 4.5 cm. Shape: Lanceolate. Apex: Acute. Base: Attenuate. Margin: Entire; slightly undulate. Texture, upper and lower surfaces: Smooth, glabrous. Venation pattern: Parallel. Color: Developing and fully developed foliage, upper surface: Close to 137A; slightly glossy. Developing and fully developed foliage, lower surface: Close to 137B. Venation: Upper surface, close to 137A; lower surface, color to 137B.

Flower description:

*Flower type and habit.*—Single cup-shaped flowers arranged in compound umbels. Perianth segments separate. Freely and continuously flowering. Flowers not persistent.

*Natural flowering season.*—Flowering continuously during the spring in The Netherlands.

*Fragrance.*—None detected.

*Flower longevity on the plant.*—About four weeks.

*Flower longevity as a cut flower.*—About 16 days.

*Flower buds* (*showing color*).—Length: About 3 to 5 cm. Diameter: About 1 to 2 cm. Shape: Roughly ovoid. Color: Yellowish.

*Umbel length.*—About 15 to 20 cm.

*Umbel diameter.*—About 20 to 25 cm.

*Number of flowers per umbel.*—About 6 to 10.

*Flower length* (*height*).—About 6 to 6.5 cm.

*Flower diameter.*—About 7 to 8 cm.

*Flower depth.*—About 5.5 to 6 cm.

*Perianth.*—Arrangement: Six arranged in two whorls, each whorl with two lateral and one median segments. Size, inner perianth segments: Length: Laterals, about 7 to 7.5 cm; median, 6 to 6.5 cm. Width, laterals and median: About 1.5 to 2 cm. Size, outer perianth segments: Length: laterals and median: About 6.5 to 7 cm. Width, laterals and median: About 3 to 3.5 cm. Shape, inner perianth, all segments: Oblanceolate. Shape, outer perianth, all segments: Obovate. Apex, inner perianth, all segments: Acute. Apex, outer perianth, all segments: Bracket-shaped. Base, inner and outer perianths, all segments: Attenuate. Margin, inner and outer perianths, all segments: Entire; weakly undulate. Texture, inner and outer perianths, all segments: Smooth, glabrous; velvety. Color, inner perianth: When opening and fully opened, laterals and median, upper surface: 14A; towards the apex, 33A; spots and stripes, close to 187A. When opening and fully opened, laterals and median, lower surface: 14A; towards the apex, 33A. Color, outer perianth: When opening and fully opened, laterals and median, upper surface: 14A; towards the apex, 33A with green tip. When opening and fully opened, laterals and median, lower surface: 14A; towards the apex, 33A with green tip and venation.

*Peduncles.*—Length: About 4 to 5 cm. Diameter: About 2 to 3 mm. Strength: Strong. Angle: About 20 to 30° from vertical. Texture: Smooth, glabrous. Color: Close to 137A.

*Pedicels.*—Length: About 1.5 to 2.5 cm. Diameter: About 2 to 3 mm. Strength: Strong. Angle: About 20° from vertical. Texture: Smooth, glabrous. Color: Close to 137A.

*Reproductive organs.*—Stamens: Quantity per flower: Six. Anther shape: Elliptical. Anther length: About 8 mm. Anther diameter: About 3 mm. Anther color: Close to 153B. Pollen amount: Scarce. Pollen color: Close to 153D. Pistils: Quantity per flower: One. Style length: About 5.5 to 6 cm. Style color: Orange. Ovary color: Close to 144A.

*Fruit.*—Shape: Globular. Color: Brownish.

Disease/pest resistance: Plants of the new *Alstroemeria* have not been observed to be resistant to pathogens and pests common to *Alstroemerias.*

Temperature tolerance: Plants of the new *Alstroemeria* have been observed to tolerate temperatures from −5 to 40° C.

It is claimed:

1. A new and distinct cultivar of *Alstroemeria* plant named 'Zalsamano', as illustrated and described.

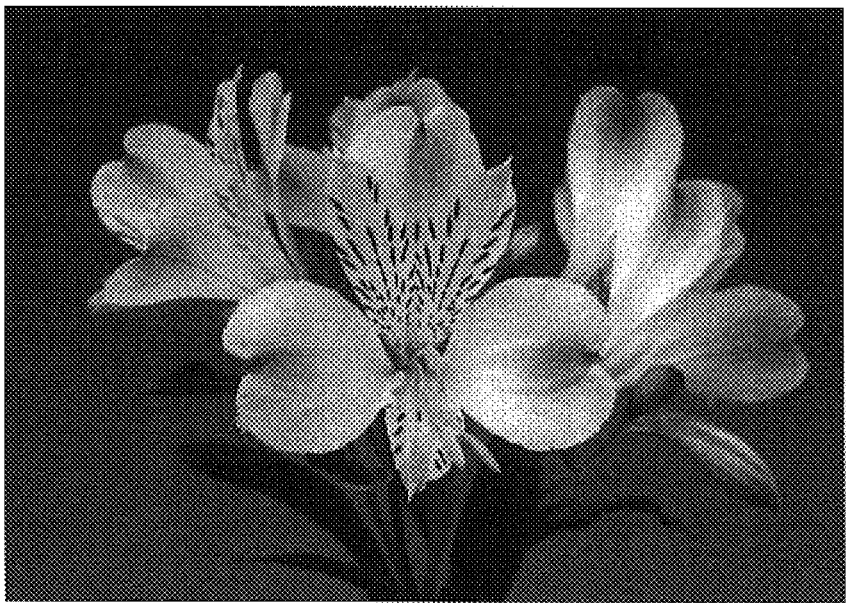

* * * * *